(12) United States Patent
Shelton et al.

(10) Patent No.: US 12,685,865 B2
(45) Date of Patent: Jul. 21, 2026

(54) SYSTEMS AND METHODS FOR TREATING OBSTRUCTIVE SLEEP APNEA WITH AUTOMATIC STARTS AND STOPS

(71) Applicant: The Alfred E. Mann Foundation for Scientific Research, Valencia, CA (US)

(72) Inventors: Brian Shelton, Ventura, CA (US); Robert J. Greenberg, Los Angeles, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 199 days.

(21) Appl. No.: 18/394,314

(22) Filed: Dec. 22, 2023

(65) Prior Publication Data

US 2024/0261574 A1      Aug. 8, 2024

Related U.S. Application Data

(60) Provisional application No. 63/483,686, filed on Feb. 7, 2023.

(51) Int. Cl.
*A61N 1/36* (2006.01)

(52) U.S. Cl.
CPC ....... *A61N 1/36139* (2013.01); *A61N 1/3601* (2013.01); *A61N 1/3611* (2013.01); *A61N 1/3615* (2013.01); *A61N 1/36175* (2013.01)

(58) Field of Classification Search
CPC .......... A61B 2562/0219; A61B 5/1116; A61B 5/113; A61B 5/4809; A61B 5/4818;
(Continued)

(56) References Cited

U.S. PATENT DOCUMENTS

2012/0192874 A1* 8/2012 Bolea ................... A61N 1/3601
128/202.16
2014/0228905 A1* 8/2014 Bolea ........................ A61F 5/56
607/42
(Continued)

FOREIGN PATENT DOCUMENTS

WO 2021/016562 A1 1/2021
WO 2021016558 A1 1/2021
WO 2021/242633 A1 12/2021

OTHER PUBLICATIONS

International Search Report and Written Opinion issued in International Application No. PCT/US2023/085770, mailed May 7, 2024, 21 pages.

(Continued)

*Primary Examiner* — George Manuel
(74) *Attorney, Agent, or Firm* — ARENTFOX SCHIFF LLP

(57) ABSTRACT

The present disclosure generally relates to systems and methods for detecting and/or treating obstructive sleep apnea (OSA) experienced by a subject, using one or more implanted or external sensors. In some aspects, the systems and methods described herein are configured to classify the human subject as being awake or asleep by comparing a calculated standard deviation and/or variance of one or more respiratory parameters against a predetermined threshold and to control the delivery of stimulation based on this classification.

29 Claims, 5 Drawing Sheets

(58) Field of Classification Search
CPC .... A61B 5/686; A61N 1/3601; A61N 1/3611;
A61N 1/36139; A61N 1/3615; A61N
1/36175; A61N 1/36
See application file for complete search history.

(56) References Cited

U.S. PATENT DOCUMENTS

| | | | |
|---|---|---|---|
| 2015/0094962 A1* | 4/2015 | Hoegh | G16H 50/30 |
| | | | 702/19 |
| 2015/0224307 A1* | 8/2015 | Bolea | A61N 1/36057 |
| | | | 607/42 |
| 2016/0354602 A1 | 12/2016 | Keenan et al. | |
| 2019/0160282 A1 | 5/2019 | Dieken et al. | |
| 2021/0228872 A1 | 7/2021 | Scheiner et al. | |
| 2022/0134103 A1 | 5/2022 | Elyahoodayan et al. | |
| 2022/0160295 A1 | 5/2022 | Christopherson et al. | |

OTHER PUBLICATIONS

Invitation to Pay Additional Fees received for PCT Patent Application No. PCT/US2023/085770, mailed on Mar. 15, 2024, 13 pages.

\* cited by examiner

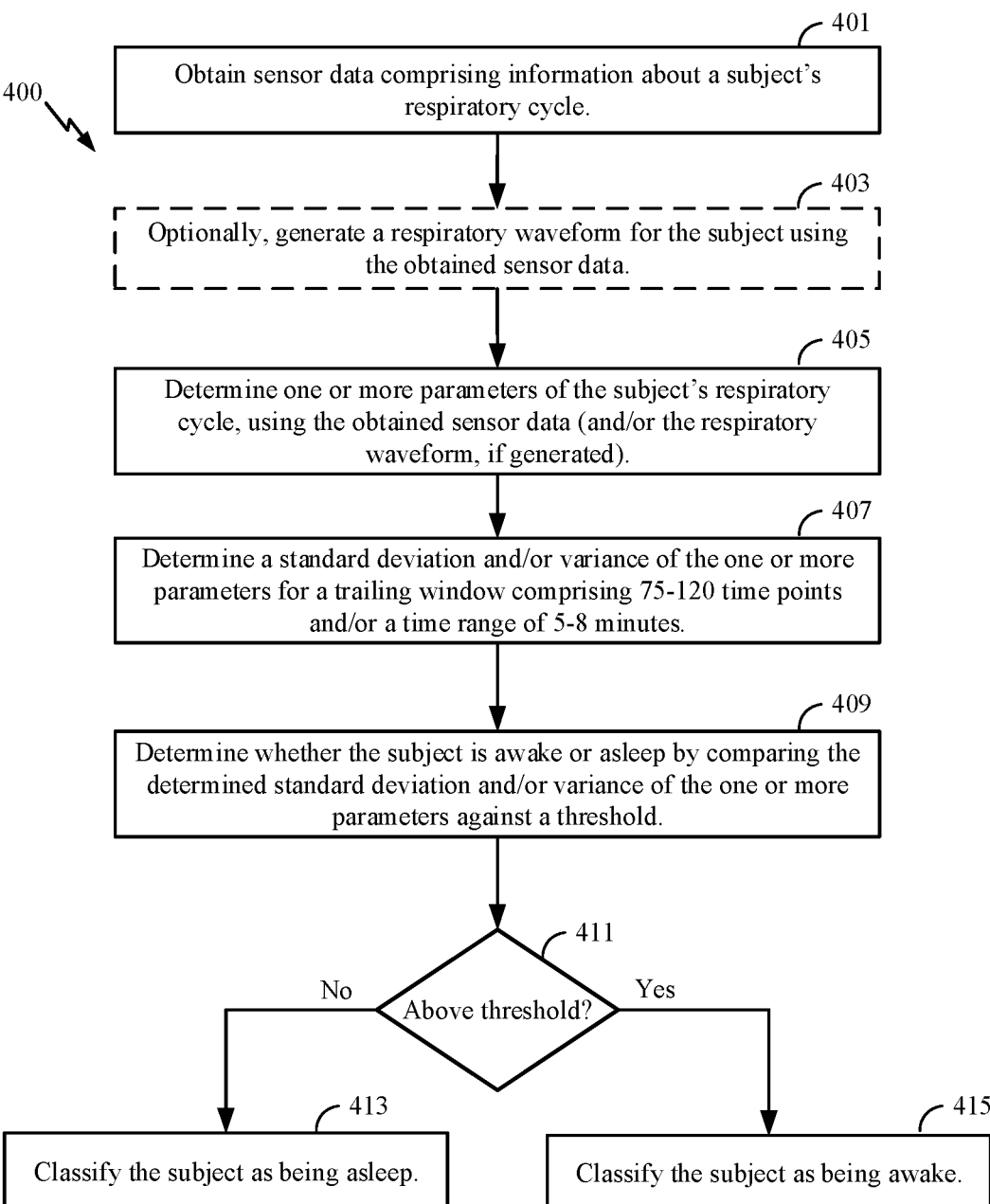

400

401

Obtain sensor data comprising information about a subject's respiratory cycle.

403

Optionally, generate a respiratory waveform for the subject using the obtained sensor data.

405

Determine one or more parameters of the subject's respiratory cycle, using the obtained sensor data (and/or the respiratory waveform, if generated).

407

Determine a standard deviation and/or variance of the one or more parameters for a trailing window comprising 75-120 time points and/or a time range of 5-8 minutes.

409

Determine whether the subject is awake or asleep by comparing the determined standard deviation and/or variance of the one or more parameters against a threshold.

411

No                Above threshold?                Yes

413

Classify the subject as being asleep.

415

Classify the subject as being awake.

FIG. 4

SYSTEMS AND METHODS FOR TREATING OBSTRUCTIVE SLEEP APNEA WITH AUTOMATIC STARTS AND STOPS

CROSS-REFERENCE TO RELATED APPLICATION

This application claims the benefit of U.S. Provisional Application No. 63/483,686, which was filed on Feb. 7, 2023, and is expressly incorporated by reference herein in its entirety.

TECHNICAL FIELD

The present disclosure generally relates to systems and methods for detecting apnea and/or hypopnea using one or more sensors, and methods of treating medical conditions related thereto.

BACKGROUND

Obstructive Sleep Apnea ("OSA") is a sleep disorder involving obstruction of the upper airway during sleep. The obstruction of the upper airway may be caused by the collapse of or increase in the resistance of the pharyngeal airway, often resulting from tongue obstruction. The obstruction of the upper airway may be caused by reduced genioglossus muscle activity during the deeper states of NREM sleep. Obstruction of the upper airway may cause breathing to pause during sleep. Cessation of breathing may cause a decrease in the blood oxygen saturation level, which may eventually be corrected when the person wakes up and resumes breathing. The long-term effects of OSA include high blood pressure, heart failure, strokes, diabetes, headaches, and general daytime sleepiness and memory loss, among other symptoms.

OSA is extremely common, and may have a prevalence similar to diabetes or asthma. Over 100 million people worldwide suffer from OSA, with about 25% of those people being treated. Continuous Positive Airway Pressure (CPAP) is a conventional therapy for people who suffer from OSA. More than five million patients own a CPAP machine in North America, but many do not comply with use of these machines because they cover the mouth and nose and, hence, are cumbersome and uncomfortable.

Neurostimulators may be used to open the upper airway as a treatment for alleviating apneic events. Such therapy may involve stimulating the nerve fascicles of the hypoglossal nerve ("HGN") that innervate the intrinsic and extrinsic muscles of the tongue in a manner that prevents retraction of the tongue which would otherwise close the upper airway during the inspiration period of the respiratory cycle. For example, current stimulator systems may be used to stimulate the trunk of the HGN with a nerve cuff electrode. However, these systems do not provide a sensor or sensing capabilities, and therefore, the stimulation delivered to the HGN trunk is not synchronized to the respiratory cycle or modulated based upon respiratory events experienced by the subject being treated, nor are such systems capable of adjusting stimulation based on the position of the subject being treated or other conditional triggers.

BRIEF SUMMARY

Ideally, a system for treating OSA should be able to account for the position of the subject being treated (e.g., in order pause or deactivate stimulation if a subject wakes during the night and sits up or stands). In some aspects, such systems may be further configured to resume stimulation when the subject returns to a supine, prone, or lateral recumbent position. The use of positional data obtained from one or more sensors (e.g., an inertial measurement unit, "IMU") may be paired with a timer or clock to provide a more sophisticated system wherein triggers are only active during particular time windows, or to allow for stimulation to be activated, deactivated, or titrated after a preset time following the detection of a change in position. In still further aspects, a system for treating OSA may be configured to combine positional data, a timer (or clock), and respiration variability data obtained from one or more sensors to determine whether a subject is asleep or awake. Such systems could use this additional data to tailor treatment, e.g., by activating, pausing, or auto-titrating settings such as stimulation intensity (e.g., by adjusting the pulse amplitude and/or pulse width of stimulation) in response to positional changes, respiratory cycle variability, and/or information about the time of day. In doing so, such systems would provide better patient care and provide a tool for monitoring the effectiveness of different therapy regiments or parameters, increasing the likelihood of a positive therapeutic outcome for the subject being treated.

The present disclosure addresses these and other shortcomings by providing OSA stimulation systems that can accurately detect and/or monitor the position and respiratory cycle of a subject being treated using one or more implanted or external sensors incorporated into or in communication with the system. Such systems may advantageously be used to provide tailored treatment for a subject, to evaluate different stimulation regimens or parameters, and/or additional functionality compared to current systems, among other benefits which will become apparent in view of the following description and the accompanying figures. For example, the present disclosure provides systems and methods wherein stimulation is activated (or paused) based upon the position of the subject or a determination as to the sleep stage (e.g., awake or asleep) of the subject. Such systems offer various advantages (e.g., increased convenience and options for therapeutic treatment), among other benefits as shall be described in further detail herein.

In a first general aspect, the disclosure provides a system for treating OSA in a human subject, comprising: one or more sensors, wherein each sensor is configured to collect sensor data indicative of respiratory activity and/or a physical state of the human subject when placed on, in proximity to, or implanted in, the human subject, wherein the one or more sensors comprise an inertial measurement unit (IMU) implanted in the human subject; and a controller comprising a processor and memory, communicatively linked to the one or more sensors and configured to: receive the sensor data from the one or more sensors, determine a position of the human subject using the IMU; and a stimulation system, communicatively linked to the controller and configured to deliver stimulation to a nerve which innervates an upper airway muscle of the human subject; wherein the controller is configured to activate, pause, and/or adjust the delivery of stimulation system based on a) preset schedule and/or b) the determined position of the human subject.

In some aspects, the IMU is an accelerometer. In some aspects, the controller is configured to stop the delivery of stimulation when the human subject is determined to be in a upright, standing, or sitting position.

In some aspects, the controller is configured to: maintain a real-time clock; temporarily pause the delivery of stimulation when the human subject is determined to have switched to an upright, standing, and/or sitting position during a preset time range; and to resume the delivery of stimulation when the human subject is determined to have returned to a supine, prone and/or lateral recumbent position.

In some aspects, the preset schedule comprises a) a time of day to enter a first mode of operation, b) a time of day to exit the first mode of operation, and c) a first delay timer setting comprising an amount of time to wait before activating the delivery of stimulation, after entering the first mode of operation; and the first mode of operation comprises a state wherein the controller is configured to activate the delivery of stimulation when the human subject is determined to have entered a supine, prone and/or lateral recumbent position, after the first delay time has elapsed.

In some aspects, the controller is configured to gradually increase a pulse amplitude of the delivered stimulation, upon activation.

In some aspects, the controller is further configured to determine the position of the human subject periodically while in the first mode of operation and to enter a second mode of operation when the human subject is determined to have switched to a upright, standing, or sitting position; and the second mode of operation comprises a state wherein the controller is configured to pause the delivery of stimulation, and to resume the delivery of stimulation after the human subject is determined to have returned to a supine, prone and/or lateral recumbent position.

In some aspects, the controller is configured to resume the delivery of stimulation in the second mode of operation after a preset second delay timer.

In some aspects, the controller is configured to cause the stimulation system to deliver stimulation to the nerve which innervates an upper airway muscle of the human subject: a) after determining that the human subject has transitioned to a supine position from a prone or lateral position; b) after determining that the human subject is asleep and in a supine position; and/or c) after determining that the human subject is asleep and has remained in a supine position for a preset minimum amount of time (e.g., for at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes, or for an amount of time within a range defined by any pair of the foregoing points). In each case, stimulation may begin immediately or after a preset delay (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes). In some aspects, the controller may be configured to initiate stimulation after the conditions for a), b), and/or c) are satisfied, at a preset point in the respiration cycle of the human subject. For example, the controller may be configured to initiate stimulation at the start, end, or a midpoint in the next respiration cycle of the human subject after the conditions for a), b), and/or c) are satisfied.

In some aspects, the controller is configured to determine that the subject has rolled on their back based on the sensor data collected by the one or more sensors.

In some aspects, the controller is configured to cause the stimulation system to deliver stimulation to the nerve which innervates an upper airway muscle of the human subject only while the human subject is in a supine position.

In some aspects, the controller is configured to allow a clinician and/or the human subject to select one or more settings for the delivery of stimulation, wherein the one or more settings comprise a setting allowing or prohibiting the delivery of the stimulation based on a position of the human subject.

In some aspects, the one or more settings comprise a setting allowing or prohibiting the delivery of the stimulation when the human subject is determined to be in a supine, prone, and/or lateral position.

In a second general aspect, the disclosure provides a system for treating OSA in a human subject, comprising: one or more sensors, wherein each sensor is configured to collect sensor data indicative of respiratory activity and/or a physical state of the human subject when placed on, in proximity to, or implanted in, the human subject; and a controller comprising a processor and memory, communicatively linked to the one or more sensors and configured to receive the sensor data from the one or more sensors, determine one or more respiratory parameters for the human subject, using the sensor data, calculate a standard deviation and/or a variance of the one or more respiratory parameters over a trailing window comprising at least, at most, about or exactly 75-120 time points and/or a time range of at least, at most, about or exactly 5-8 minutes, and classify the human subject as being awake or asleep by comparing the calculated standard deviation and/or a variance against a predetermined threshold; and a stimulation system, communicatively linked to the controller and configured to deliver stimulation to a nerve which innervates an upper airway muscle of the human subject based on the classification by the controller.

In some aspects, the controller is configured to determine one or more respiratory parameters for the human subject by generating a respiratory waveform using the sensor data and determining period and/or amplitude values for one or more respiratory cycles.

In some aspects, the trailing window comprises 75, 80, 85, 90, 95, 100, 105, 110, 115, or 120 time points, or an amount of time points within a range bounded by any of the foregoing amounts. In some aspects, the trailing window comprises 5, 5.25, 5.5, 5.75, 6, 6.25, 6.5, 6.75, 7, 7.25, 7.5, 7.75 or 8 minutes, or an amount of time within a range bounded by any of the foregoing amounts.

In some aspects, the comparison of the calculated standard deviation and/or a variance against a predetermined threshold comprises using a cost-minimizing function to compare the standard deviation and/or variance against scored data obtained from a polysomnogram (PSG) taken during a sleep study.

In some aspects, the predetermined threshold is a mean value that was generated using sensor data indicative of respiratory activity and/or a physical state of the human subject, previously collected from the human subject. In some aspects, the threshold is a mean value that was generated based on sensor data collected when the human subject was a) asleep, or b) awake. In some aspects, the threshold is a mean value that was generated based on sensor data collected when the human subject was determined to be a) in a supine, prone, or lateral recumbent position, or b) in an upright, standing, or sitting position, optionally wherein the mean value is based on sensor data collected at a time of day within a predetermined time range.

In some aspects, one or more components and/or functions of the systems described herein may be implemented by software, hardware, or a combination thereof.

In a third general aspect, the disclosure provides methods for treating OSA using any of the systems described herein. For example, in some aspects a method for treating obstructive sleep apnea (OSA) in a human subject comprising: collecting sensor data indicative of respiratory activity and/or a physical state of the human subject when placed on, in proximity to, or implanted in, the human subject, using one or more sensors, wherein the one or more sensors comprise an inertial measurement unit (IMU) implanted in the human subject; receiving, by a controller comprising a processor and memory and communicatively linked to the one or more sensors, the sensor data from the one or more sensors; determining a position of the human subject using the IMU; and delivering stimulation to a nerve which innervates an upper airway muscle of the human subject, using a stimulation system communicatively linked to the controller; wherein the controller is configured to activate, pause, and/or adjust the delivery of stimulation system based on a) preset schedule and/or b) the determined position of the human subject.

In other aspects, a method for treating obstructive sleep apnea (OSA) in a human subject may comprise: collecting sensor data indicative of respiratory activity and/or a physical state of the human subject when placed on, in proximity to, or implanted in, the human subject, using one or more sensors; receiving, by a controller comprising a processor and memory and communicatively linked to the one or more sensors, the sensor data from the one or more sensors; determining one or more respiratory parameters for the human subject, using the sensor data; calculating a standard deviation and/or a variance of the one or more respiratory parameters over a trailing window comprising at least, at most, about or exactly 75-120 time points and/or a time range of at least, at most, about or exactly 5-8 minutes; classifying the human subject as being awake or asleep by comparing the calculated standard deviation and/or a variance against a predetermined threshold; and delivering stimulation to a nerve which innervates an upper airway muscle of the human subject, using a stimulation system communicatively linked to the controller, based on the classification by the controller.

It is expressly understood that any structure, element, parameter, or function described in the foregoing summary of exemplary aspects may be incorporated into any other exemplary aspect listed above or otherwise disclosed herein. For example, a sensor or parameter used in one exemplary system may be integrated into another exemplary system, without departing from the spirit of the present disclosure. Such permutations are contemplated but not expressly recited in the interests of brevity. Similarly, any structure, element, parameter, or function described in connection with an exemplary aspect may be removed or omitted in still further exemplary aspects.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

FIG. 4 is a conceptual flow diagram summarizing a general method for classifying the level of wakefulness of a subject (e.g., asleep versus awake) according to the present disclosure. As described herein, this classification may be used as a parameter when determining whether to deliver stimulation (or the amplitude and/or pulse width of stimulation).

DETAILED DESCRIPTION

Figure 1:
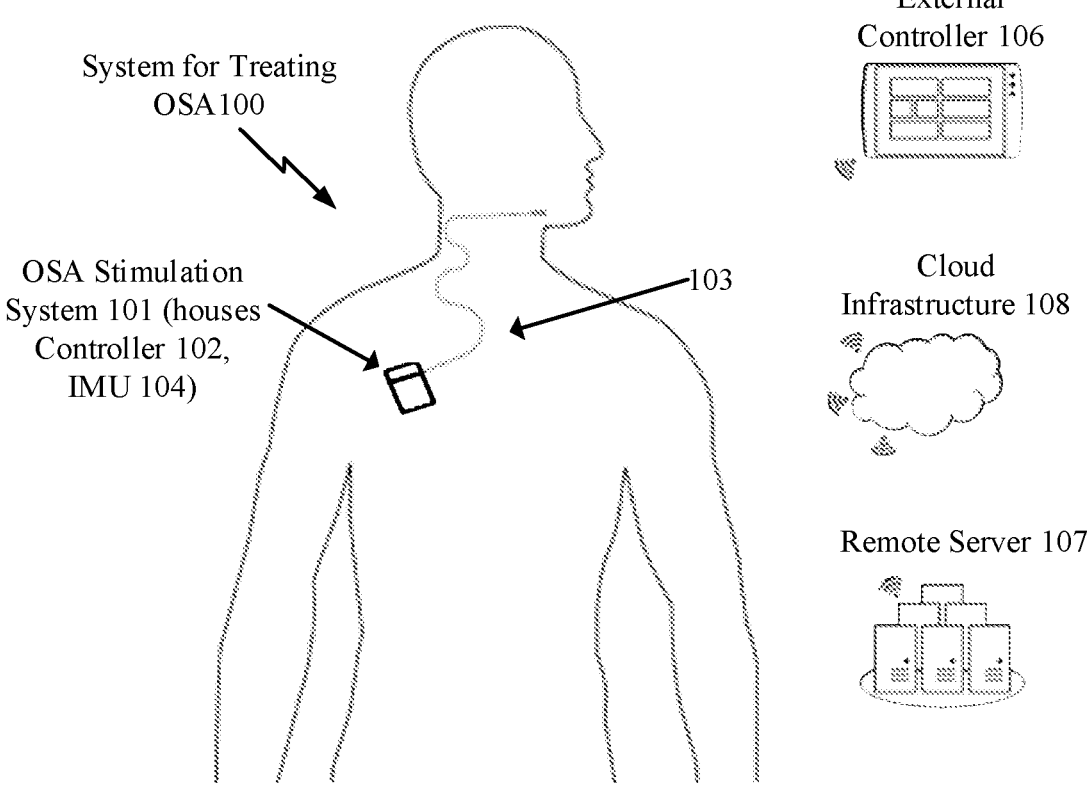
FIG. 1 is a diagram illustrating an exemplary embodiment of a system for treating OSA using a controller configured to detect and/or monitor the subject's position and respiratory cycle variability based upon sensor data. In this example, the system comprises an external sensor, as well as an implanted sensor integrated into the housing of an implanted OSA stimulation system. Optional cloud-based components of a system according to the disclosure are also illustrated.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

As noted above, the present disclosure is generally directed to systems and methods for treating OSA based upon positional data, respiratory cycle variability, and/or timing data detected (or monitored) by one or more sensors. Sleep, and more specifically quality of sleep, is now recognized as critical to human health. Lack of sleep, or poor sleep contributes significantly not only to poor cognitive performance, but also to a host of human health conditions including hypertension, heart failure, cognitive disorders, diabetes, and many others. Accordingly, there exists a need in the art for the systems described herein, which provide new tools for monitoring and treating OSA, and which offer improved accuracy and convenience compared to current systems.

As used herein, the terms "apnea" and "hypopnea" are to be understood with reference to the current American Academy of Sleep Medicine ("AASM") definitions for these terms. The AASM guidelines define a "hypopnea" (in an adult patient) as a ≥30% reduction in nasal pressure, nasal airflow, or other some other hypopnea sensor that last for ≥10 seconds and that corresponds to an oxygen desaturation event. A hypopnea oxygen desaturation event can either be defined as a ≥3% drop from the pre-event baseline with an arousal or as a ≥4% drop from the pre-event baseline without consideration of an arousal. The AASM guidelines further define an "apnea" as a cessation of airflow for ≥10 seconds.

Current systems for the detection of apnea and hypopnea suffer from various drawbacks. For example, the detection of hypopneas and apneas typically requires a combination of a nasal flow (or nasal temperature) sensor, a respiration effort (e.g., a thoracic RIP band) sensor, and an oximeter. Wearing a nasal flow sensor, a nasal temperature sensor, and a thoracic RIP band can be uncomfortable and requires user intervention. This is not only a patient burden, but can also disturb sleep. Moreover, such systems often depend upon a wired communication system (adding to patient discomfort) or a wireless system that may not fail to capture data from the various sensors or which may rely upon additional electronic devices that may not be present or which could have become disconnected from the system.

In contrast, the OSA stimulation system described herein simplify and improve upon existing designs by incorporating additional sensor functionality into one or more implanted components of the system. Such systems may utilize, e.g., a combination of sensors configured to detect and or collect data regarding the respiratory cycle of a subject being treated (e.g., using an IMU and/or a microphone), positional data for the subject (e.g., using an IMU), and/or one or more additional sensors, such as a heart rate sensor (e.g., to detect Heart Rate Variability, "HRV"), an electrocardiogram ("ECG") sensor, or an optical $SpO_2$ sensor. In some aspects, such systems may also incorporate a clock (e.g., a real-time clock) or timer to provide timing information (e.g., regarding the time of data or time elapsed since a given event or trigger), allowing for further configuration options (e.g., to activate stimulation after a preset timer elapses following a triggering event, or to allow for alternative stimulation modes during different time ranges). The systems described herein may be used to activate, pause, or auto-titrate stimulation intensity (e.g. stimulation current, pulse width, or duty cycle) when particular conditions are detected and/or during particular time ranges.

A system according to the disclosure may utilize one or more implanted sensors (e.g., incorporated into an implanted OSA stimulation system), without the need for sensor data collected from any external sensors. However, in some aspects, an implanted device may not have the sensors required to measure all of the parameters described herein. In such cases, one or more external sensors may be used to supplement the dataset available to the system, e.g., to include actigraphy, heart rate, blood oxygen level, blood pressure, EEG, single or low channel EEG, in-ear EEG, other brain activity like FNIRS (functional near infra-red spectroscopy), EMG, eye movement (EOG), and environmental data such a temperature, humidity, extraneous noise, etc. In that sense, it is understood that systems according to the disclosure are modular in that they may take into account sensor data collected using any combination of implanted and external sensors, and may further be configured to take into account parameters based on environmental data (e.g., temperature) and biomarker concentrations or amounts (e.g., determined based upon an analysis of a subject's blood).

In some aspects, the present disclosure contemplates using data from an active implantable device with or without supplemental data from one or more external devices to determine the position and/or sleep stage (e.g., awake or asleep) of the subject being treated. In some aspects, artificial intelligence, machine learning, and/or deep learning may be used to compare data collected from a subject with generalized datasets to develop or inform one or more classification algorithms (e.g., to allow for the detection and/or classification of respiratory events such as apneas and hypopneas). In another aspect, the data collected from a patient may be compared with data collected during a PSG study for a single (or multiple) nights to inform/train the respiratory event classification algorithm for that patient. In another aspect, data collected from an implanted sensor and one or more external sensors, obtained from several patients, can be compared with PSG data from these patients to more broadly inform a population-based respiratory event classification algorithm.

FIG. 1 is a diagram illustrating an exemplary embodiment of a system for treating OSA (100) using a controller configured to detect and/or monitor a subject's respiratory cycle variability and/or position based upon sensor data. In this example, the system comprises a controller (102) and an implanted IMU (104) integrated into the housing of an implanted OSA stimulation system (101). The controller (102) and the implanted IMU (104) may be used to detect and/or monitor the subject's respiration cycle and positional changes. An optional external controller (106) and cloud-based components (107, 108) of a system according to the disclosure are also illustrated.

In this example, the system comprises one implanted sensor (the IMU, 104). The implanted sensor (104) is integrated into the housing of the OSA stimulation system (101). In this case, the implanted controller (102) is capable of wireless communication with the optional external controller (106) and with one or more external sensors, e.g., a smart watch containing a heart rate or oxygen level sensor (not shown). The external controller (106) may be, e.g., a dedicated controller with a text-based or graphical user interface, or software executed on a user's smart phone, tablet, computer, or other multi-purpose electronic device. The implanted controller (102) and/or the external controller (106) may be configured to communicate with one or more local, remote, or cloud-based servers. For example, in this case the external controller (106) is capable of communicating with a remote server (107) via intermediary cloud-based infrastructure (106).

In some aspects the external controller (106) may be configured to execute a user application (109) configured to communicate with a clinical application (110) (e.g., executed on the remote server, 107) via an intervening cloud infrastructure (108), allowing a remote clinician to interact with the external controller (106) or the implanted controller (102). This configuration may allow for a clinician to view sensor data and/or respiratory cycle data for the subject stored on the internal controller (102) or the external controller (106), and to view and/or modify one or more settings of the OSA stimulation system. For example, the clinician may be able to edit the settings stored on the external controller (106), which may in turn be transmitted to the implanted controller (102) in order to modify the treatment regimen or stimulation parameters applied by the OSA stimulation system (101).

In this exemplary embodiment, the implanted OSA stimulation system comprises a housing that includes both an implantable pulse generator ("IPG"), at least one implanted sensor (an IMU, 104) and a controller (102) configured to handle signal processing and storage, operation of the OSA stimulation system, and wireless communication between the OSA stimulation system (101) and a user application (109) executed on the external controller (106). The OSA stimulation system (101) further includes one or more electrodes (103) to deliver stimulation to one or more nerves which innervate an upper airway muscle of the human subject. As described herein, the system (100) may be configured to adjust one or more stimulation parameters based upon the position of the subject and/or respiratory cycle data for the subject (e.g., respiratory cycle variability above a preset threshold may be used to determine that a subject is awake). In some aspects, the implanted controller (102) may be configured to detect and classify such respiratory events using a trained classifier executed by the implanted controller (102). The trained classifier may be used to analyze sensor data collected from any number of implanted or external sensors, using any of the techniques described herein. In alternative aspects, the classification may be performed by an external controller (106) or by a local, remote, or cloud-based server (e.g., it may be advantageous to offload the computation required for a classification to an external device, rather than using the power and limited processing capabilities of an implanted controller (102).

Figure 2:
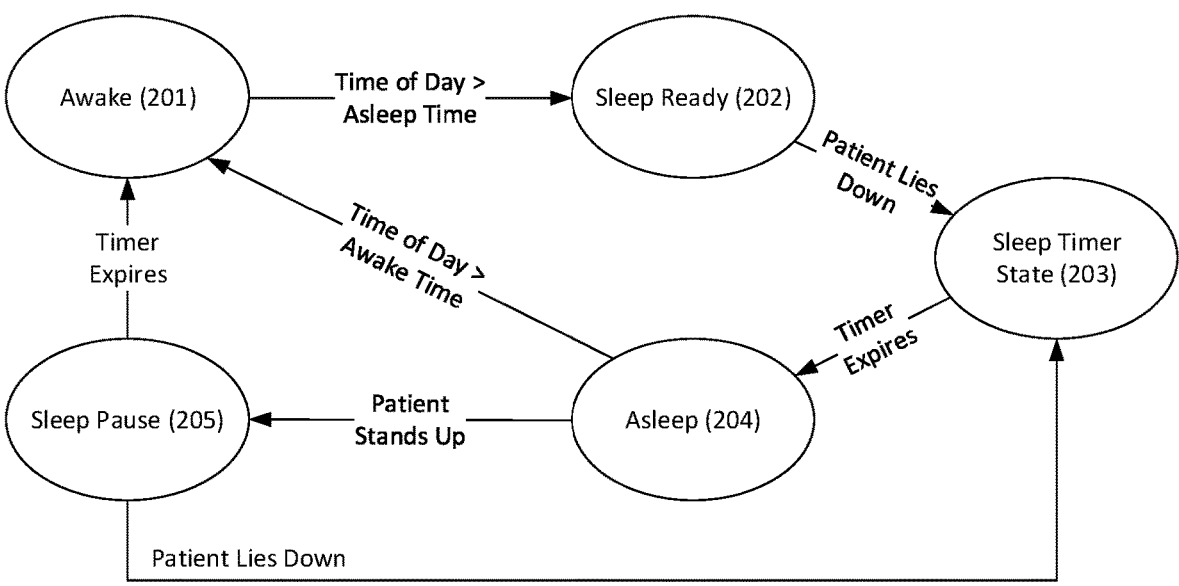
FIG. 2 is a process state diagram for an exemplary system for treating OSA, in accordance with the present disclosure. In this example, the state of the system shifts based upon the time of day and the position of the human subject, among other parameters.

FIG. 2 is a process state diagram for an exemplary system for treating OSA, in accordance with the present disclosure. As illustrated by this figure, a system according to the disclosure may utilize positional data for the subject (e.g., obtained using an implanted or external IMU or other sensor) and time data (e.g., monitored using a real-time clock or timer) to control stimulation. In this example, the system operates in and switches between five states. In the first state (201), the subject is determined to be awake. The system is configured to allow a user (or clinician) to set a time of day when the subject expects to sleep (the "asleep time" setting shown in this figure). When a clock or timer integrated into the OSA system (e.g., maintained by the controller) determines that the time of day has passed this preset time, the system may switch to the second state (202). In this state ("sleep ready") it is presumed that the subject has or will soon go to sleep. At this point, the system is configured to monitor the position of the subject and to progress to the next state when it is determined that the subject has entered a supine, prone, or lateral recumbent position (e.g., when the subject lies down). Upon entering this state (203), the clock or timer may be used by the controller to determine when a preset timer has elapsed (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes, or a time within a range bounded by any of the foregoing values). When this timer ends, the system is configured to enter a fourth state (204) wherein it is assumed that the subject is sleeping. At this point, the system may be configured to deliver stimulation, e.g., periodically or upon the detect of respiratory events such as apneas or hypopneas. In the event that the subject is determined to have switched to an upright position (e.g., by standing or sitting up), the system may switch to the fifth state ("sleep pause," 205). Upon entering this state, stimulation may be temporarily paused until the subject is determined to have returned to a supine, prone, or lateral recumbent position (i.e., returning to state 203). Alternatively, upon entering state 205, the system may be configured to return to state 201 if a preset timer elapses prior to a positional change that would have triggered a return to state 203. In some aspects, a stimulation system according to the disclosure may be programmed to switch between any or all of the states shown in FIG. 2 (i.e., in other embodiments the states shown in this diagram may be reordered). Moreover, in some aspects systems may be configured to activate, deactivate, pause, adjust, or titrate stimulation during any of these states.

Figure 3:
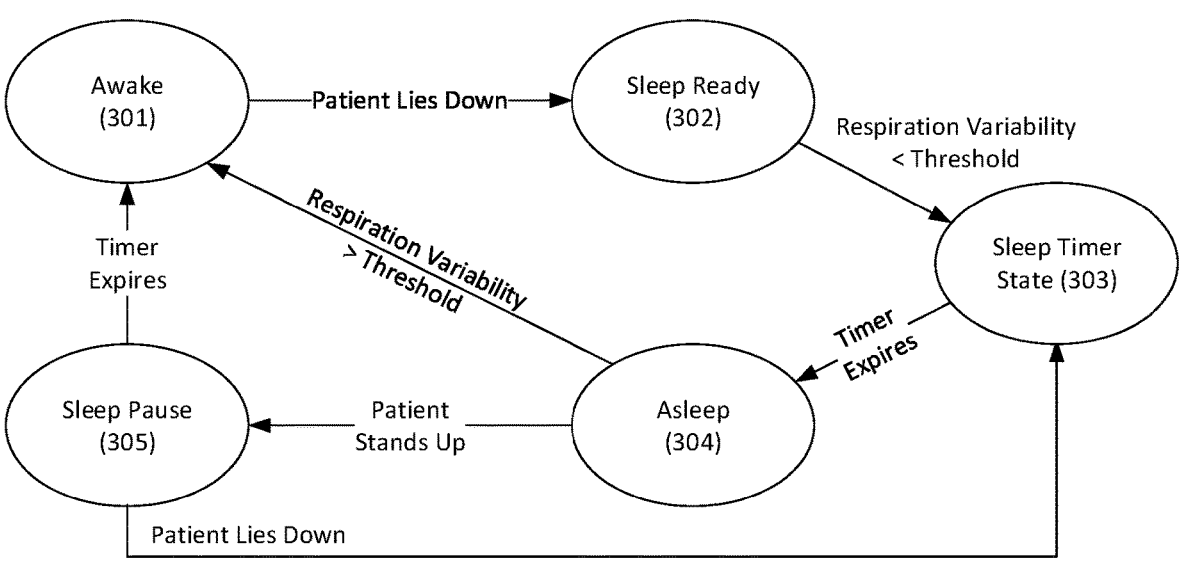
FIG. 3 is a process state diagram for another exemplary system for treating OSA, in accordance with the present disclosure. In this example, the state of the system shifts based upon respiratory cycle variability and the position of the human subject, among other parameters.

FIG. 3 is a process state diagram for another exemplary system for treating OSA, in accordance with the present disclosure. As illustrated by this figure, a system according to the disclosure may utilize positional data for the subject (e.g., obtained using an implanted or external IMU or other sensor), time data (e.g., monitored using a real-time clock or timer), and respiratory cycle variability data (e.g., detected using an IMU or other sensor) to control stimulation. In this example, the system operates in and switches between five states. In the first state (301), the subject is determined to be awake. When the system determines that the subject has switched to a prone, supine, or lateral recumbent position, the system may switch to the second state (302). In this state ("sleep ready") it is presumed that the subject has or will soon go to sleep. At this point, the system is configured to monitor the respiratory cycle of the subject and to progress to the next state when it is determined that the respiratory cycle variability of the subject has fallen below a preset threshold. Upon entering this state (203), a clock or timer may be used by the controller to determine when a preset timer has elapsed (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes, or a time within a range bounded by any of the foregoing values). When this timer ends, the system is configured to enter a fourth state (304) wherein it is assumed that the subject is sleeping. At this point, the system may be configured to deliver stimulation, e.g., periodically or upon the detect of respiratory events such as apneas or hypopneas. In the event that the subject is determined to have switched to an upright position (e.g., by standing or sitting up), the system may switch to the fifth state ("sleep pause," 305). Upon entering this state, stimulation may be temporarily paused until the subject is determined to have returned to a supine, prone, or lateral recumbent position (i.e., returning to state 303). Alternatively, upon entering state 305, the system may be configured to return to state 301 if a preset timer elapses prior to a positional change that would have triggered a return to state 303. In some aspects, a stimulation system according to the disclosure may be programmed to switch between any or all of the states shown in FIG. 3 (i.e., in other embodiments the states shown in this diagram may be reordered). Moreover, in some aspects systems may be configured to activate, deactivate, pause, adjust, or titrate stimulation during any of these states.

In some aspects, a system according to this aspect may utilize a real-time clock, as noted above, which may be used to start and stop the stimulator based on the time of day. The subject being treated, or a medical professional, may set a start time for stimulation (e.g., in the evening) and the time that stimulation would stop (e.g., in the morning). In some aspects of this implementation, the subject would be able to set these times for each day of the week, e.g., to account for their usual or preferred sleep time range. This could be further improved by using an accelerometer (e.g., an IMU in incorporated into the housing of the implanted stimulator or otherwise communicatively linked with the stimulation system). Using an IMU, the implant could determine when the patient arises and lays back down, as described above. Doing so would allow the implant to pause stimulation when the patient arises in the middle of the night and resume stimulation when the patient lies back down. There is no harm in starting stimulation while the subject is still awake. However, sometimes the subject will notice when stimulation abruptly starts a find this sensation to be uncomfortable. To prevent this, the stimulation pulse amplitude may be slowly ramped up to maximum intensity over several minutes (e.g., over 1, 2, 3, 4, 5, 6, 7, 8, 9 or 10 minutes).

FIG. 4 is a conceptual flow diagram summarizing another general method for treating OSA using an exemplary system according to the present disclosure. As shown by this diagram, such method may begin with the collection of sensor data comprising information about a subject's respiratory cycle (401). Optionally, this respiratory cycle data may be used to generate a respiratory waveform for the subject (403). At the next step (405), one or more respiratory parameters of the subject's respiratory cycle may be determined using the collected sensor data (and/or the respiratory waveform, if generated). For example, the period or amplitude of one or more respiratory cycles may be detected, measured, and/or stored by the system (e.g., in memory integrated into an implanted stimulation system or an external controller). Next, the system may measure the variability of the one or more respiratory cycle parameters over time. For example, as shown by step 407 the system may determine the standard deviation and/or variance of the one or more respiratory parameters (e.g., of the respiratory cycle timing and/or amplitude) over a trailing window comprising 75-120 time points and/or a time range of 5-8 minutes. In other aspects, the trailing window may comprise a number of time points comprising any integer between 75-120 or a number within a subrange bounded by any pair of integers selected from that range. Similarly, in some aspects the trailing window may comprise a time range of 1, 2, 3, 4, 5, 6, 7, 8, 9, 10, 11, 12, 13, 14, or 15 minutes, or a time within a range bounded by any of the foregoing time points). The system may proceed to determine whether the subject is awake or asleep by comparing the determined standard deviation and/or variance of the one or more respiratory parameters against a preset threshold (step 409). The system may be configured to classify the subject as asleep if the variability is below the preset threshold (413), or awake if the variability is above the preset threshold (415).

In some aspects, the present threshold may be configured for each subject. This may be done by using a cost-minimizing function to compare the standard deviation or variance of the one or more respiratory parameters against the scored data obtained from a polysomnogram (PSG) taken during a sleep study, or it may be performed dynamically after the sleep study by using the time-of-day and the subject's position to roughly approximate sleep. For example, the system may be configured to measure the respiration rate variability during a time period time when a subject is laying down during the subject's self-defined typical sleep hours. The system may further be configured to determine that a subject is asleep based on a threshold parameter (e.g., determined based on an average of these respiration rate variabilities or to the average plus a predefined number of standard deviations (e.g., 1, 2, or 3). This threshold may then be used to determine when the patient is asleep using data collected from the one or more sensors of the system. In some aspects, the system may be further configured to modify the collection of respiration rate variabilities, e.g., by filtering out those at the beginning and/or end of the night, or by eliminating outliers.

Similarly, the distribution of respiration rate variabilities can be measured during the subject's defined daytime period while the subject is vertical. The average of these variabilities or the average minus a number of standard deviations (e.g., 1, 2, or 3) may be used to set a threshold. This threshold may then be used to determine when a patient is awake using data collected from the one or more sensors of the system. In some aspects, the system may be further configured to modify the collection of respiration rate variabilities, e.g., by filtering out those at the beginning and/or end of the night, or by eliminating outliers.

In many cases, the awake and asleep thresholds will be significantly different. The system may thus be configured to select a mid-point between these two thresholds in order to determine if a patient is awake or asleep. In some cases, the two ranges will overlap. However, if there is a gap between the two ranges, using both thresholds will result in the asleep/awake detection some hysteresis.

Upon classifying the subject as being asleep (413), the system may be configured to activate, deactivate, or titrate stimulation, either immediately or following an additional trigger condition. For example, stimulation may be triggered after a timer has elapsed or after a determination is made as to the subject's position (e.g., upon a determination that the subject is in a supine, prone, or lateral recumbent position, using an IMU or other sensor). In some aspects, the stimulation intensity may be titrated upwards (e.g., by adjusting the pulse amplitude and/or pulse width of stimulation) when the subject is classified as being asleep, immediately or after a timer has elapsed and/or another trigger is satisfied (e.g., a positional change), as noted above.

Figure 5:
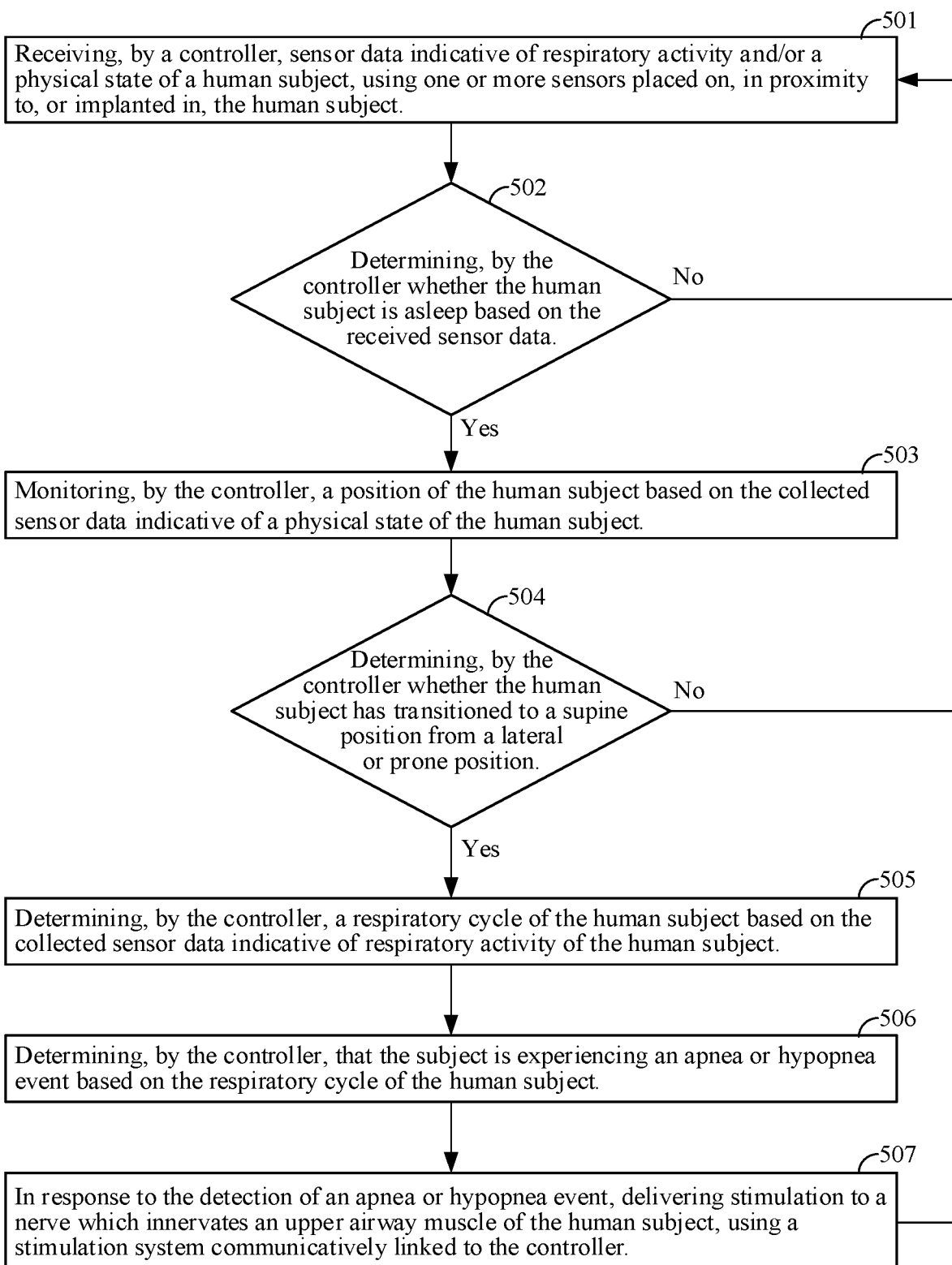
FIG. 5 is a conceptual flow diagram summarizing a general method for treating OSA using the systems described herein. In this exemplary aspect, stimulation is only initiated when the subject is determined to have rolled onto their back (e.g., by transitioning to a supine position from another position).

FIG. 5 is a conceptual flow diagram summarizing another general method for treating OSA using an exemplary system according to the present disclosure. As shown by this diagram, systems according to the disclosure may include a controller configured to receive sensor data indicative of respiratory activity and/or a physical state of a human subject, collected using one or more sensors placed on, in proximity to, or implanted in, the human subject (501). Sensor data may be obtained from each sensor periodically, continuously, or as needed. The one or more sensors may comprise an IMU (e.g., an accelerometer and/or a gyroscope) or any other sensors described herein. For example, the one or more sensors may comprise an IMU, a microphone, a heart rate sensor, an ECG sensor, and/or an optical SpO$_2$ sensor.

The controller may be configured to determine whether the human subject is awake or asleep based on the received sensor data (502). For example, the controller may be configured to continuously (or periodically) determine the position of the subject and to classify the subject as awake or asleep based at least in part on this positional data. A subject that is upright (e.g., standing or sitting) is unlikely to be asleep, whereas a subject that is in a prone, supine, or lateral recumbent position may be asleep. In some aspects, the controller may be configured to take into account sensor data indicative of respiratory activity when making this determination. For example, inspiration and expiration length, and respiratory cycle variability, are useful biomarkers for detecting whether a subject is asleep or awake. Additional sensor data, e.g., heart rate data, may also or alternatively be used to determine whether a subject is asleep. It is advantageous to determine whether a subject is awake; if so, there would normally be no need for an OSA treatment to be delivered.

In this particular example, when a subject is found to be asleep, the system is configured to monitor the subject's position (503) and to determine whether the subject has transitioned to a supine position from a lateral or prone position (e.g., detecting that the subject has "rolled over" on their back) (504). This determination may be made, e.g., based on the sensor data indicative of the physical state of the subject collected using the IMU or another sensor. If a transition is not detected, the system returns to monitoring the respiratory activity and/or the physical state of the subject (501). Alternatively, if a transition is detected, the controller of the system proceeds to determine a respiratory cycle of the human subject based on the collected sensor data indicative of respiratory activity (505). Note that in this example, step 503 occurs only upon the determination that the subject is asleep, and step 505 occurs only upon the determination of a transition to a supine position. This configuration may be preferred in some contexts, as it conserves power (e.g., by avoiding the need to process sensor data. However, in alternative aspects, it is understood that the position and/or the respiratory cycle of the subject may be continuously or periodically monitored regardless of whether the subject is determined to be asleep or to have transitioned into any particular position.

In any case, the controller may be configured to determine that the subject is experiencing an apnea or hypopnea event based on the respiratory cycle of the human subject (506). For example, variability in one or more parameters of the respiratory cycle (e.g., the period or amplitude of inspiration and/or expiration) compared to a baseline control, a historical respiratory cycle, an average respiratory cycle, etc. may be used to determine that an apnea or hypopnea event has or is currently occurring. In such cases, the controller may be configured to cause a communicatively linked stimulation system to deliver electrical stimulation to at least one nerve innervating an upper airway muscle of the human subject (e.g., the HGN) (507). After delivering stimulation, the system may return to monitoring the respiratory activity and/or the physical state of the human subject (501). Note that in other aspects, an apnea or hypopnea event may be determined using additional or alternative sensor data. For example, heart rate data and/or positional data may be used to supplement or make this determination (e.g., heart rate variability or a sudden increase in heart rate may be indicative of an apnea or hypopnea event). Similarly, the detection of an abrupt positional change (e.g., the detection of a heaving motion of the chest or abdomen of the subject may indicative an apnea or hypopnea event). Thus, it should be appreciated that the detection of an apnea or hypopnea event may be based on sensor data collected from any of the various sensors described herein.

In some aspects, systems according to the present disclosure may allow a user or a clinician to modify one or more settings governing the delivery of stimulation. For example, as explained above a controller of the present systems may be configured to deliver stimulation according to a preset schedule and/or based on the position of the subject being treated. In some aspects, either of these parameters may be adjusted (e.g., via a dedicated external controller available to a clinician, technician, or the subject being treated, which is capable of wirelessly communicating with the controller of the system). In some aspects, the controller may be configured to only allow the delivery of stimulation when a subject is determined to be in one or more positions, and/or to prohibit the delivery of stimulation when a subject is determined to be in one or more specified positions. For example, a clinician may wish to configure the system to only allow for stimulation to be delivered when the subject is determined to be in a prone, lateral recumbent, or supine position, or to prohibit the delivery of stimulation when the subject is determined to be in an upright (e.g., sitting or standing) position.

In some aspects, the controller may also, or alternatively, allow one to modify a preset schedule that determines when stimulation can be delivered. For example, the controller may allow one to specify time range(s) when stimulation may be delivered (e.g., during the night) and/or to prohibit stimulation during specified time range(s) (e.g., during the day, when a subject is likely to be awake). Embodiments that allow one to limit stimulation only to certain positions and/or time schedules may advantageously reduce the likelihood of stimulation being delivered at an incorrect time. For example, a subject lying in a supine or lateral recumbent position during the afternoon may be awake (e.g., reading or engaged in another activity). If the subject were to breath irregularly for some reason (e.g., due to a respiratory illness), it is possible that stimulation may be triggered due to a false positive detection of an apnea or hypopnea event. However, a system that allows one to limit the delivery of stimulation to particular time range(s) or based on the detection of specific position(s) may reduce or limit the likelihood of such errors. Similarly, in some aspects, systems according to the disclosure may be configured to allow a subject to manually disable stimulation temporarily or for a preset time (e.g., using a dedicated controller or other electronic device capable of wirelessly communicating with the controller).

The present disclosure provides the following non-limiting numbered embodiments, which illustrate aspects of the systems and methods disclosed herein. These embodiments are to be viewed as a non-exhaustive list of examples and it is understood that any of the features, structural elements, parameters, and functions of these embodiments may be combined (or removed) to produce further embodiments that still fall within the scope of the present disclosure.

Embodiment 1. A system for treating OSA in a human subject, comprising: one or more sensors, wherein each sensor is configured to collect sensor data indicative of respiratory activity and/or a physical state of the human subject when placed on, in proximity to, or implanted in, the human subject, wherein the one or more sensors comprise an IMU implanted in the human subject; and a controller comprising a processor and memory, communicatively linked to the one or more sensors and configured to: receive the sensor data from the one or more sensors, determine a position of the human subject using the IMU; and a stimulation system, communicatively linked to the controller and configured to deliver stimulation to a nerve which innervates an upper airway muscle of the human subject; wherein the controller is configured to activate, pause, and/or adjust the delivery of stimulation based on a) preset schedule and/or b) the determined position of the human subject.

Embodiment 2. The system of Embodiment 1, wherein the IMU is an accelerometer.

Embodiment 3. The system of any one of Embodiments 1-2, wherein the controller is configured to stop and/or prevent the delivery of stimulation when the human subject is determined to be in an upright, standing, or sitting position.

Embodiment 4. The system of any one of Embodiments 1-3, wherein the controller is configured to: maintain a real-time clock; temporarily pause the delivery of stimulation when the human subject is determined to have switched to an upright, standing, and/or sitting position during a preset time range; and to resume the delivery of stimulation when the human subject is determined to have returned to a supine, prone and/or lateral recumbent position.

Embodiment 5. The system of any one of Embodiments 1-5, wherein the preset schedule comprises a) a time of day to enter a first mode of operation, b) a time of day to exit the first mode of operation, and c) a first delay timer setting comprising an amount of time to wait before activating the delivery of stimulation, after entering the first mode of operation; and the first mode of operation comprises a state wherein the controller is configured to activate the delivery of stimulation when the human subject is determined to have entered a supine, prone and/or lateral recumbent position, after the first delay time has elapsed.

Embodiment 6. The system of any one of Embodiments 1-5, wherein the controller is configured to gradually increase a pulse amplitude of the delivered stimulation, upon activation.

Embodiment 7. The system of any one of Embodiments 1-5, wherein the controller is further configured to determine the position of the human subject periodically while in the first mode of operation and to enter a second mode of operation when the human subject is determined to have switched to a upright, standing, or sitting position; and the second mode of operation comprises a state wherein the controller is configured to pause the delivery of stimulation, and to resume the delivery of stimulation after the human subject is determined to have returned to a supine, prone and/or lateral recumbent position.

Embodiment 8. The system of Embodiment 7, wherein the controller is configured to resume the delivery of stimulation in the second mode of operation after a preset second delay timer.

Embodiment 9. The system of any one of Embodiments 1-8, wherein the controller is configured to cause the stimulation system to deliver stimulation to the nerve which innervates an upper airway muscle of the human subject: a) after determining that the human subject is asleep and has transitioned to a supine position from a prone or lateral position; b) after determining that the human subject is sleeping and in supine position; and/or c) after determining that the human subject is asleep and has remained in a supine position for a preset minimum amount of time.

Embodiment 10. The system of any one of Embodiments 1-9, wherein the controller is configured to determine that the subject has rolled on their back based on the sensor data collected by the one or more sensors.

Embodiment 11. The system of any one of Embodiments 1-9, wherein the controller is configured to cause the stimulation system to deliver stimulation to the nerve which innervates an upper airway muscle of the human subject only while the human subject is in a supine position.

Embodiment 12. The system of any one of Embodiments 1-11, wherein the controller is configured to allow a clinician and/or the human subject to select one or more settings for the delivery of stimulation, wherein the one or more settings comprise a setting allowing or prohibiting the delivery of the stimulation based on a position of the human subject.

Embodiment 13. The system of Embodiment 12, wherein the one or more settings comprise a setting allowing or prohibiting the delivery of the stimulation when the human subject is determined to be in a supine, prone, and/or lateral position.

Embodiment 14. The system of any one of Embodiments 12-13, wherein the one or more settings comprise a) a duty cycle of the stimulation; and/or b) a pulse amplitude of the stimulation.

Embodiment 15. The system of Embodiment 13, wherein the one or more settings comprise a) a duty cycle of the stimulation; and/or b) a pulse amplitude of the stimulation.

Embodiment 16. A method for treating OSA in a human subject comprising: collecting sensor data indicative of respiratory activity and/or a physical state of the human subject when placed on, in proximity to, or implanted in, the human subject, using one or more sensors, wherein the one or more sensors comprise an IMU implanted in the human subject; receiving, by a controller comprising a processor and memory and communicatively linked to the one or more sensors, the sensor data from the one or more sensors; determining a position of the human subject using the IMU; and delivering stimulation to a nerve which innervates an upper airway muscle of the human subject, using a stimulation system communicatively linked to the controller; wherein the controller is configured to activate, pause, and/or adjust the delivery of stimulation based on a) preset schedule and/or b) the determined position of the human subject.

Embodiment 17. The method of Embodiment 16, wherein the IMU is an accelerometer.

Embodiment 18. The method of any one of Embodiments 16-17, wherein the controller is configured to stop and/or prevent the delivery of stimulation when the human subject is determined to be in an upright, standing, or sitting position.

Embodiment 19. The method of any one of Embodiments 16-18, wherein the controller is configured to: maintain a real-time clock; temporarily pause the delivery of stimulation when the human subject is determined to have switched to an upright, standing, and/or sitting position during a preset time range; and to resume the delivery of stimulation when the human subject is determined to have returned to a supine, prone and/or lateral recumbent position.

Embodiment 20. The method of any one of Embodiments 16-19, wherein the preset schedule comprises a) a time of day to enter a first mode of operation, b) a time of day to exit the first mode of operation, and c) a first delay timer setting comprising an amount of time to wait before activating the delivery of stimulation, after entering the first mode of operation; and the first mode of operation comprises a state wherein the controller is configured to activate the delivery of stimulation when the human subject is determined to have entered a supine, prone and/or lateral recumbent position, after the first delay time has elapsed.

Embodiment 21. The method of any one of Embodiments 16-20, wherein the controller is configured to gradually increase a pulse amplitude of the delivered stimulation, upon activation.

Embodiment 22. The method of any one of Embodiments 16-20, wherein the controller is further configured to determine the position of the human subject periodically while in the first mode of operation and to enter a second mode of operation when the human subject is determined to have switched to a upright, standing, or sitting position; and the second mode of operation comprises a state wherein the controller is configured to pause the delivery of stimulation, and to resume the delivery of stimulation after the human subject is determined to have returned to a supine, prone and/or lateral recumbent position.

Embodiment 23. The method of any one of Embodiments 16-20, wherein the controller is configured to resume the delivery of stimulation in the second mode of operation after a preset second delay timer.

Embodiment 24. The method of any one of Embodiments 16-24, wherein the controller is configured to cause the stimulation system to deliver stimulation to the nerve which innervates an upper airway muscle of the human subject only after determining that the human subject is asleep and has transitioned to a supine position from a prone or lateral position.

Embodiment 25. The method of any one of Embodiments 16-24, wherein the controller is configured to determine that the subject has rolled on their back based on the sensor data collected by the one or more sensors.

Embodiment 26. The method of any one of Embodiments 16-24, wherein the controller is configured to cause the stimulation system to deliver stimulation to the nerve which innervates an upper airway muscle of the human subject only while the human subject is in a supine position.

Embodiment 27. The method of any one of Embodiments 16-26, wherein the controller is configured to allow a clinician and/or the human subject to select one or more settings for the delivery of stimulation, wherein the one or more settings comprise a setting allowing or prohibiting the delivery of the stimulation based on a position of the human subject.

Embodiment 28. The method of Embodiment 27, wherein the one or more settings comprise a setting allowing or prohibiting the delivery of the stimulation when the human subject is determined to be in a supine, prone, and/or lateral position.

Embodiment 29. A system for treating OSA in a human subject, comprising: one or more sensors, wherein each sensor is configured to collect sensor data indicative of respiratory activity and/or a physical state of the human subject when placed on, in proximity to, or implanted in, the human subject; and a controller comprising a processor and memory, communicatively linked to the one or more sensors and configured to receive the sensor data from the one or more sensors, determine one or more respiratory parameters for the human subject, using the sensor data, calculate a standard deviation and/or a variance of the one or more respiratory parameters over a trailing window comprising at least, at most, about or exactly 75-120 time points and/or a time range of at least, at most, about or exactly 5-8 minutes, and classify the human subject as being awake or asleep by comparing the calculated standard deviation and/or a variance against a predetermined threshold; and a stimulation system, communicatively linked to the controller and configured to deliver stimulation to a nerve which innervates an upper airway muscle of the human subject based on the classification by the controller.

Embodiment 30. The system of Embodiment 29, wherein the controller is configured to determine the one or more respiratory parameters for the human subject by generating a respiratory waveform using the sensor data and determining period and/or amplitude values for one or more respiratory cycles.

Embodiment 31. The system of any one of Embodiments 29-30, wherein the trailing window comprises 75, 80, 85, 90, 95, 100, 105, 110, 115, or 120 time points, or an amount of time points within a range bounded by any of the foregoing amounts.

Embodiment 32. The system of any one of Embodiments 29-30, wherein the trailing window comprises 5, 5.25, 5.5, 5.75, 6, 6.25, 6.5, 6.75, 7, 7.25, 7.5, 7.75 or 8 minutes, or an amount of time within a range bounded by any of the foregoing amounts.

Embodiment 33. The system of any one of Embodiments 29-32, wherein the comparison of the calculated standard deviation and/or a variance against a predetermined threshold comprises using a cost-minimizing function to compare the standard deviation and/or variance against scored data obtained from a PSG taken during a sleep study.

Embodiment 34. The system of any one of Embodiments 29-33, wherein the predetermined threshold is a mean value that was generated using sensor data indicative of respiratory activity and/or a physical state of the human subject, previously collected from the human subject.

Embodiment 35. The system of Embodiment 34, wherein the threshold is a mean value that was generated based on sensor data collected when the human subject was a) asleep, or b) awake.

Embodiment 36. The system of Embodiment 34, wherein the threshold is a mean value that was generated based on sensor data collected when the human subject was determined to be a) in a supine, prone, or lateral recumbent position, or b) in an upright, standing, or sitting position, optionally wherein the mean value is based on sensor data collected at a time of day within a predetermined time range.

Embodiment 37. A method for treating OSA in a human subject comprising: collecting sensor data indicative of respiratory activity and/or a physical state of the human subject when placed on, in proximity to, or implanted in, the human subject, using one or more sensors; receiving, by a controller comprising a processor and memory and communicatively linked to the one or more sensors, the sensor data from the one or more sensors; determining one or more respiratory parameters for the human subject, using the sensor data; calculating a standard deviation and/or a variance of the one or more respiratory parameters over a trailing window comprising at least, at most, about or exactly 75-120 time points and/or a time range of at least, at most, about or exactly 5-8 minutes; classifying the human subject as being awake or asleep by comparing the calculated standard deviation and/or a variance against a predetermined threshold; and delivering stimulation to a nerve which innervates an upper airway muscle of the human subject, using a stimulation system communicatively linked to the controller, based on the classification by the controller.

Embodiment 38. The method of Embodiment 37, wherein the controller is configured to determine the one or more respiratory parameters for the human subject by generating a respiratory waveform using the sensor data and determining period and/or amplitude values for one or more respiratory cycles.

Embodiment 39. The method of any one of Embodiments 37-38, wherein the trailing window comprises 75, 80, 85, 90, 95, 100, 105, 110, 115, or 120 time points, or an amount of time points within a range bounded by any of the foregoing amounts.

Embodiment 40. The method of any one of Embodiments 37-38, wherein the trailing window comprises 5, 5.25, 5.5, 5.75, 6, 6.25, 6.5, 6.75, 7, 7.25, 7.5, 7.75 or 8 minutes, or an amount of time within a range bounded by any of the foregoing amounts.

Embodiment 41. The method of any one of Embodiments 37-40, wherein the comparison of the calculated standard deviation and/or a variance against a predetermined threshold comprises using a cost-minimizing function to compare the standard deviation and/or variance against scored data obtained from a PSG taken during a sleep study.

Embodiment 42. The method of any one of Embodiments 37-41, wherein the predetermined threshold is a mean value that was generated using sensor data indicative of respiratory activity and/or a physical state of the human subject, previously collected from the human subject.

Embodiment 43. The method of Embodiment 42, wherein the threshold is a mean value that was generated based on sensor data collected when the human subject was a) asleep, or b) awake.

Embodiment 44. The method of Embodiment 42, wherein the threshold is a mean value that was generated based on sensor data collected when the human subject was determined to be a) in a supine, prone, or lateral recumbent position, or b) in an upright, standing, or sitting position, optionally wherein the mean value is based on sensor data collected at a time of day within a predetermined time range.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators-such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A implantable system for treating obstructive sleep apnea (OSA) in a human subject, comprising:
   an inertial measurement unit (IMU); and
   a controller communicatively linked to the IMU and configured to:
      receive sensor data from the IMU, and
      determine a position of the human subject from the sensor data; and
   a stimulation system, communicatively linked to the controller and configured to deliver stimulation to a nerve which innervates an upper airway muscle of the human subject;
   wherein the stimulation system is configured to activate the delivery of stimulation to the nerve when the controller detects a transition in the position of the human subject.

2. The system of claim 1, wherein the IMU is an accelerometer.

3. The system of claim 1, wherein the controller is further configured to cause the stimulation system to stop or prevent the delivery of stimulation when the human subject is determined to be in an upright, standing, or sitting position.

4. The system of claim 1, wherein the controller is further configured to:
   maintain a real-time clock;
   temporarily pause the delivery of stimulation when the human subject is determined to have switched to an upright, standing, or sitting position during a preset time range; and to resume the delivery of stimulation when the human subject is determined to have returned to a supine, prone or lateral recumbent position.

5. The system of claim 1, wherein the controller is further configured to cause the stimulation system to activate the delivery of stimulation based on a preset schedule,
   wherein the preset schedule comprises a) a time of day to enter a first mode of operation, b) a time of day to exit the first mode of operation, and c) a first delay timer setting comprising an amount of time to wait before activating the delivery of stimulation, after entering the first mode of operation; and
   the first mode of operation comprises a state wherein the controller is further configured to cause the stimulation system to activate the delivery of stimulation when the human subject is determined to have entered a supine, prone or lateral recumbent position, after the first delay time has elapsed.

6. The system of claim 5, wherein the controller is further configured to cause the stimulation system to gradually increase a pulse amplitude of the delivered stimulation, upon activation.

7. The system of claim 5, wherein the controller is further configured to determine the position of the human subject periodically while in the first mode of operation and to enter a second mode of operation when the human subject is determined to have switched to an upright, standing, or sitting position; and the second mode of operation comprises a state wherein the controller is configured to cause the stimulation system to pause the delivery of stimulation, and to resume the delivery of stimulation after the human subject is determined to have returned to a supine, prone or lateral recumbent position.

8. The system of claim 7, wherein the controller is further configured to cause the stimulation system to resume the delivery of stimulation in the second mode of operation after a preset second delay timer.

9. The system of claim 1, wherein the controller is further configured to cause the stimulation system to deliver stimulation to the nerve which innervates an upper airway muscle of the human subject:

a) after determining that the human subject is asleep and detecting transition from a supine position from a prone or lateral position; or b) after determining that the human subject is asleep and detecting that the human subject has remained in a supine position for a minimum duration.

10. The system of claim 9, wherein the controller is further configured to determine that the human subject has rolled on their back based on the sensor data collected by one or more sensors.

11. The system of claim 9, wherein the controller is further configured to cause the stimulation system to deliver stimulation to the nerve which innervates an upper airway muscle of the human subject only while the human subject is in a supine position.

12. The system of claim 1, wherein the controller is further configured to receive, from a clinician or the human subject, a selection of one or more settings for the delivery of stimulation, wherein the one or more settings comprise a setting allowing or prohibiting the delivery of the stimulation based on a position of the human subject.

13. The system of claim 12, wherein the one or more settings comprise a setting allowing or prohibiting the delivery of the stimulation when the human subject is determined to be in a supine, prone, or lateral position.

14. The system of claim 12, wherein the one or more settings comprise a) a duty cycle of the stimulation; or b) a pulse amplitude of the stimulation.

15. The system of claim 1, wherein the controller is further configured to cause the stimulation system to activate the delivery of stimulation to the nerve after a time delay from when the controller detects that the subject is in a recumbent position during a preset time window and pause the delivery of stimulation to the nerve when the subject transitions to an upright position.

16. A method for treating obstructive sleep apnea (OSA) in a human subject comprising:

collecting sensor data indicative of respiratory activity or a physical state of the human subject using at least an inertial measurement unit (IMU) implanted in the human subject;

receiving the sensor data from the IMU;

determining a position of the human subject from the sensor data;

delivering stimulation to a nerve which innervates an upper airway muscle of the human subject using a stimulation system; and activating, using the stimulation system, the delivery of stimulation to the nerve upon a detection of a transition in the position of the human subject.

17. The method of claim 16, wherein the IMU is an accelerometer.

18. The method of claim 16, further comprising: stopping or preventing the delivery of stimulation when the human subject is determined to be in an upright, standing, or sitting position.

19. The method of claim 16, further comprising:

maintaining a real-time clock;

temporarily pausing the delivery of stimulation when the human subject is determined to have switched to an upright, standing, or sitting position during a preset time range; and to resuming the delivery of stimulation when the human subject is determined to have returned to a supine, prone or lateral recumbent position.

20. The method of claim 16, further comprising:

activating the delivery of stimulation based on a preset schedule, wherein the preset schedule comprises a) a time of day to enter a first mode of operation, b) a time of day to exit the first mode of operation, and c) a first delay timer setting comprising an amount of time to wait before activating the delivery of stimulation, after entering the first mode of operation; and the first mode of operation comprises a state to activate the delivery of stimulation when the human subject is determined to have entered a supine, prone or lateral recumbent position, after the first delay time has elapsed.

21. The method of claim 20, further comprising: gradually increasing a pulse amplitude of the delivered stimulation, upon activation.

22. The method of claim 20, further comprising: determining the position of the human subject periodically while in the first mode of operation and to enter a second mode of operation when the human subject is determined to have switched to an upright, standing, or sitting position; and the second mode of operation comprises a state to pause the delivery of stimulation, and to resume the delivery of stimulation after the human subject is determined to have returned to a supine, prone or lateral recumbent position.

23. The method of claim 22, further comprising: resuming the delivery of stimulation in the second mode of operation after a preset second delay timer.

24. The method of claim 16, further comprising: causing the stimulation system to deliver stimulation to the nerve which innervates an upper airway muscle of the human subject only after determining that the human subject is asleep and has transitioned to a supine position from a prone or lateral position.

25. The method of claim 24, further comprising: determining that the subject has rolled on their back based on the collected sensor data.

26. The method of claim 24, further comprising: delivering stimulation to the nerve which innervates an upper airway muscle of the human subject only while the human subject is in a supine position.

27. The method of claim 16, further comprising: obtaining, from a clinician or the human subject, a selection of one or more settings for the delivery of stimulation, wherein the one or more settings comprise a setting allowing or prohibiting the delivery of the stimulation based on a position of the human subject.

28. The method of claim 27, wherein the one or more settings comprise a setting allowing or prohibiting the delivery of the stimulation when the human subject is determined to be in a supine, prone, or lateral position.

29. A implantable system for treating obstructive sleep apnea (OSA) in a human subject, comprising:

one or more sensors, wherein each sensor is configured to collect sensor data indicative of respiratory activity or a physical state of the human subject when placed on, in proximity to, or implanted in, the human subject; and a controller communicatively linked to the one or more sensors and configured to;

receive the sensor data from the one or more sensors, determine one or more respiratory parameters for the human subject, using the sensor data, calculate a standard deviation or a variance of the one or more respiratory parameters over a trailing window comprising 75-120 time points or a time range of 5-8 minutes, and classify the human subject as being awake or asleep by comparing the calculated standard deviation or a variance against a predetermined threshold; and a stimulation system, communicatively linked to the controller and configured to deliver stimulation to a nerve which innervates an upper airway muscle of the human subject based on the classification by the controller, wherein the controller is configured to cause the stimulation system to activate the delivery of stimulation to the nerve when the controller detects a transition in the position of the human subject.

\* \* \* \* \*